(12) United States Patent
Akechi et al.

(10) Patent No.: US 8,361,414 B2
(45) Date of Patent: Jan. 29, 2013

(54) GAS EXCHANGE CHIP

(75) Inventors: Masakazu Akechi, Kyoto (JP); Yoichi Fujiyama, Kyoto (JP); Hirohisa Abe, Kyoto (JP); Masaki Kanai, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 1197 days.

(21) Appl. No.: 11/794,728

(22) PCT Filed: Dec. 28, 2005

(86) PCT No.: PCT/JP2005/024105
§ 371 (c)(1),
(2), (4) Date: Jul. 5, 2007

(87) PCT Pub. No.: WO2006/080177
PCT Pub. Date: Aug. 3, 2006

(65) Prior Publication Data
US 2008/0085216 A1    Apr. 10, 2008

(30) Foreign Application Priority Data
Jan. 6, 2005 (JP) ................................. 2005-001845

(51) Int. Cl.
*B01L 3/00*  (2006.01)
*G01N 1/10*  (2006.01)

(52) U.S. Cl. ........ 422/503; 422/500; 422/501; 422/502; 422/504; 436/180

(58) Field of Classification Search ............ 422/100; 436/180
See application file for complete search history.

(56) References Cited

U.S. PATENT DOCUMENTS

| 4,666,860 A | 5/1987 | Blades et al. |
| 5,443,991 A | 8/1995 | Godec et al. |
| 6,130,098 A | 10/2000 | Handique et al. |

FOREIGN PATENT DOCUMENTS

| JP | 54-78898 A | 6/1979 |
| JP | 3370407 B2 | 11/2002 |
| JP | 2005-329333 A | 12/2005 |
| WO | WO-00/22436 A1 | 4/2000 |
| WO | WO-03/035229 A2 | 5/2003 |
| WO | WO-2004/059299 A1 | 7/2004 |
| WO | WO 2004059299 A1 * | 7/2004 |

OTHER PUBLICATIONS

International Search Report mailed May 15, 2006.
Supplementary European Search Report for the Application No. EP 05 84 4827 dated Sep. 3, 2008.

* cited by examiner

*Primary Examiner* — Dean Kwak
(74) *Attorney, Agent, or Firm* — Cheng Law Group, PLLC

(57) ABSTRACT

[PROBLEMS] To increase the rate of gas transfer in gas exchangers.
[MEANS FOR SOLVING PROBLEMS] A gas exchange chip comprises substrates (1,2); two flow channels (3,4) formed in the substrates (1,2) and each having an inlet port and an outlet port; and multiple grooves (9) interlinking the flow channels (3,4). The grooves (9) have the size of their sectional area predetermined and have at least a part of the internal surface thereof rendered hydrophobic so as to permit the transfer of gas component while inhibiting any liquid passage. A sample water containing carbon dioxide is caused to flow through one of the flow channels (3) while pure water is caused to flow through the other flow channel (4) to thereby transfer the carbon dioxide contained in the sample water into the pure water.

6 Claims, 6 Drawing Sheets

GAS EXCHANGE CHIP

TECHNICAL FIELD

The present invention relates to a gas exchanger for removing gas components such as oxygen and carbon dioxide gas from a liquid or transferring them into a gas or another liquid, and to a gas extraction method and a total organic carbon measuring instrument using such a gas exchanger.

BACKGROUND ART

As a gas exchanger that removes gas components from a liquid or transfers gas components to make them dissolve in a liquid, those utilizing hollow fiber membranes are used. Hollow fiber membranes are used as a module in which multiple hollow fiber membranes are bundled and caps are provided on both ends. Such module is used in such a manner that a liquid is caused to flow through the hollow fiber membranes, and a gas contained in the liquid is removed by external aspiration, or a gas is caused to blend into the liquid in the hollow fiber membranes by pressurizing an external gas (see Japanese Patent No. 3370407 publication).

One exemplary total organic carbon measuring instrument for measuring total organic carbon in a sample water is equipped with an organic compound oxidative decomposing part for converting organic carbon into carbon dioxide; a carbon dioxide extracting part for extracting carbon dioxide generated in the organic compound oxidative decomposing part into pure water; and a detecting part for detecting conductivity of pure water in the carbon dioxide extracting part for quantifying the carbon dioxide extracted in the carbon dioxide extracting part.

In such a total organic carbon measuring instrument, for transferring carbon dioxide from a sample water having been subjected to oxidation process in the organic compound oxidative decomposing part into pure water, in the carbon dioxide extracting part, the sample water and the pure water are arranged with a gas permeable membrane or a porous membrane intervened therebetween so that carbon dioxide in the sample water is transferred into the pure water via the gas permeable membrane or the porous membrane.

DISCLOSURE OF THE INVENTION

Problems to be Solved by the Invention

In a conventional gas exchanger using hollow fiber membranes, since a bundle of hollow fiber membranes is used, a long transfer time is required and gas exchange speed is decreased because a long transfer distance is required for dissolving a gas from outside of the bundle into a liquid flowing through a hollow fiber membrane in the center of the bundle of hollow fiber membranes, or for extracting a gas outside from a liquid flowing through a hollow fiber membrane in the center of the bundle of hollow fiber membranes.

Therefore, the first object of the present invention is to increase the rate of gas transfer in a gas exchanger.

When a gas permeable membrane is used in a carbon dioxide extracting part in a total organic carbon measuring instrument, a time required for transferring carbon dioxide in the carbon dioxide extracting part is long because of low transmission speed.

When a porous membrane is used in a carbon dioxide extracting part, transmission speed of carbon dioxide in the porous membrane is high. However, carbon dioxide will diffuse into the entire membrane because all of the pores existing in the porous membrane run in all directions. As a result, immediately after starting of transfer of carbon dioxide, a phenomenon occurs that concentration of transferred carbon dioxide decreases, so that a time required for causing a sample water containing carbon dioxide to flow and making concentration of carbon dioxide in the membrane constant.

Therefore, the second object of the present invention is to provide a total organic carbon measuring instrument in which rate of carbon dioxide transfer in a carbon dioxide extracting part is increased.

Means for Solving the Problems

The present invention is characterized in that gas component is transferred through grooves, each of which has an inner face which is at least partly hydrophobized and has a size of a cross section adapted to permit passage of gas component while inhibiting any liquid passage.

A first gas exchange chip of the present invention is a double-flow channel type gas exchange chip which conducts gas exchange or extraction between two flow channels. The first gas exchange chip has a substrate, two flow channels formed in the substrate, each of the flow channels having an inlet port and an outlet port; and multiple grooves interlinking the two flow channels. Each of the grooves has an inner face which is at least partly hydrophobized and has a size of a cross section set to permit passage of gas component while inhibiting any liquid passage.

In one aspect of the above, the two flow channels are disposed parallel to each other in a plane which is parallel with the surface of the substrate, and the grooves are formed in the substrate.

In another aspect of the above, the two flow channels are disposed facing each other via a membrane, and the grooves are formed by pores that penetrate the membrane and formed in such orientation that they do not cross each other.

A second gas exchange chip of the present invention is a single-flow channel type gas exchange chip which conducts gas exchange and extraction between one flow channel and outside of the substrate. The second gas exchange chip has a substrate; a flow channel formed in the substrate, the flow channel having an inlet port and an outlet port; and multiple grooves interlinking the flow channel and outside. Each of the grooves has an inner face which is at least partly hydrophobized and has a size of a cross section set to permit passage of gas component while inhibiting any liquid passage.

The grooves formed in the substrate preferably have a depth and a width of 10 μm or less, and the grooves formed in the membrane preferably have a diameter of 1 μm or less.

Conventionally, a permeable membrane is used for gas exchange or extraction. However, in the present invention, by using fine grooves in which at least a part of the inner surface is hydrophobic, gas component in a liquid or gas component which is to be dissolved in a liquid is transferred via a gas that is present in the grooves without transmission of liquid.

Preferably, both the depth and width of the flow channel are 1000 μm or less.

A gas extracting method of the present invention is carried out using a gas exchange chip of the present invention.

A first aspect of a gas extracting method using a double-flow channel type gas exchange chip is a method in which liquids are caused to flow through both of the flow channels in the double-flow channel type gas exchange chip, and gas component is transferred between the liquids in these flow channels. A concrete application thereof is a gas extracting method wherein the liquid in one of the flow channels is a sample water containing carbon dioxide, and the liquid in the other one of the flow channels is pure water, and carbon dioxide in the sample water is transferred to the pure water.

A second aspect of the gas extracting method using the double-flow channel type gas exchange chip is a method in which a liquid is caused to flow through either of the flow channels in the double-flow channel type gas exchange chip, and a gas is caused to flow through the other one of the flow channels, to thereby transfer and dissolve the gas into the liquid in the flow channel.

A third aspect of the gas extracting method using the double-flow channel type gas exchange chip is a method in which a liquid is caused to flow through either of the flow channels in the double-flow channel type gas exchange chip, and the pressure of the other one of the flow channels is reduced, to thereby transfer a gas component in the liquid in one flow channel to the other flow channel.

A first aspect of a gas extracting method using a single-flow channel type gas exchange chip is a gas extracting method in which a liquid is caused to flow through the flow channel to thereby dissolve a gas outside of the substrate into the liquid in the flow channel.

A second aspect of the gas extracting method using the single-flow channel type gas exchange chip is a gas extracting method in which a liquid is caused to flow through the flow channel, and external pressure is reduced to thereby extract gas component in the liquid in the flow channel to outside of the substrate.

The total organic carbon measuring instrument of the present invention has an organic compound oxidative decomposing part for converting organic carbon in a sample water into carbon dioxide; a carbon dioxide extracting part for extracting carbon dioxide generated in the organic compound oxidative decomposing part into pure water; and a detecting part for measuring conductivity of the pure water from the carbon dioxide extracting part after extraction of carbon dioxide for quantifying carbon dioxide extracted in the carbon dioxide extracting part, wherein the double-flow channel type gas exchange chip of the present invention is used as the carbon dioxide extracting part, and the sample water from the organic compound oxidative decomposing part is caused to flow through one of the flow channels, and the pure water is caused to flow through the other the flow channel, and the pure water passing through the gas exchange chip is fed to the detecting part.

Effect of the Invention

With the use of a gas exchange chip according to the present invention, it is possible to conduct gas exchange of a sample within a short time with a small amount of reagent, to miniaturize the instrument and reduce a consumption amount of the reagent.

By making a width and a depth of a flow channel through which a liquid flows very small as 1000 μm or less by a microfabrication technique, it is possible to shorten the distance between a groove and a flow channel through which a liquid flows, and thus to shorten the distance in which a gas contained in a liquid is transferred from the flow channel to the groove, or the distance in which a gas is transferred from the groove to a liquid in the flow channel. Since the transfer time is proportional to the square of the transfer distance, it is possible to shorten the time of transfer of the gas to be exchanged or extracted.

In the total organic carbon measuring instrument according to the present invention, since a gas exchange chip of the present invention is used as a carbon dioxide extracting part, the speed at which carbon dioxide travels via a gas in the fine groove having a hydrophobic surface is very high, so that carbon dioxide can be transferred faster than in the case using a permeable membrane.

When a porous membrane is used as a carbon dioxide extracting part, carbon dioxide diffuses in the porous membrane. However, when a membrane having a hydrophobic surface and fine pores formed so that they do not cross each other is used as a gas exchange chip of the carbon dioxide extracting part, carbon dioxide can travel without diffusing in the membrane because the fine pores do not cross each other. Therefore, the time required for making the concentration of carbon dioxide in the membrane constant is almost unneeded when a sample water containing carbon dioxide flows.

Furthermore, by making a width and a depth of a flow channel in which a sample water flows in the gas exchange chip of the carbon dioxide extracting part very small by way of a microfabrication technique, it is possible to shorten the distance between the groove and the flow channel in which the sample water flows, and to shorten the distance in which carbon dioxide contained in the sample water travels from the flow channel to the grooves, so that it is possible to shorten the time required for carbon dioxide extracted from the sample water to be transferred.

BEST MODES FOR CARRYING OUT THE INVENTION

FIG. 1A to FIG. 1B show a first embodiment of a double-flow channel type gas exchange chip, in which FIG. 1A is a plan view showing an arrangement of flow channels and grooves, and FIG. 1B is a section view along the line A-A in FIG. 1A.

Reference numerals 1, 2 denote glass substrates, for example, quartz substrates. On one side of one glass substrate 1, flow channels 3, 4 having a width and a depth of 1000 μm or less, preferably several hundred micrometers or less, are formed. On one side of the other glass substrate 2, multiple grooves 9 having hydrophobic surfaces at positions interlinking the flow channels 3, 4 are formed, and at the positions corresponding to both ends of the flow channels 3, 4, holes 5, 6, 7, 8 for use in introduction or discharge of a liquid or a gas are formed so that they penetrate the glass substrate 2.

The glass substrates 1, 2 face each other so that the surface in which the flow channels 3, 4 are formed and the surface in which the grooves 9 are formed are inside, and bonded while they are positioned so that the holes 5, 6, 7, 8 are disposed on both ends of the flow channels 3, 4, and the grooves 9 interlink the flow channels 3, 4, to form an integrated substrate.

The groove 9 has a length and a width of several hundred micrometers or less, and preferably the width and a height of 10 μm or less. When a liquid flows through one or both of the flow channels 3, 4, a gas is transferred through the grooves while no liquid enters the groove 9.

These flow channels 3, 4 and grooves 9 may be formed by a microfabrication technique using, for example, photolithography and etching, and the holes 5, 6, 7, 8 may be formed, for example, by a sand blasting method. The inner face of the groove 9 may be made hydrophobic by fluorinating the inner face of the groove, for example, by an RIE (reactive ion etching) process under flow of a fluorine compound gas such as $CHF_3$ gas or $CF_4$ gas or by decomposition of the fluorine compound by optical irradiation of an excimer laser.

The glass substrates 1, 2 may be bonded by hydrofluoric acid bonding. In hydrofluoric acid bonding, for example, a 1% hydrofluoric acid solution is interposed in the boundary surface between the glass substrates 1, 2, and left still for about 24 hours at room temperature, under a load of about 1 MPa as necessary.

FIG. 2A to FIG. 2B show a second embodiment of the double-flow channel type gas exchange chip, in which FIG. 2A is a plan view showing an arrangement of a flow channel and grooves, and FIG. 2B is a section view along the line A-A in FIG. 2A.

Substrates 17, 18 are silicone substrates. On one side of the silicon substrate 17, flow channels 19, 20 and multiple grooves 21 interlinking the flow channels 19, 20 are formed. On the other silicon substrate 18, at the positions corresponding to both ends of the flow channels 19, 20, through-holes 22, 23, 24, 25 for use in introduction or discharge of a liquid or a gas are formed.

The silicon substrates 17, 18 are opposed so that the surface in which the flow channels 19, 20 and the grooves 21 are formed are inside, and bonded while they are positioned so that the holes 22, 23, 24, 25 are disposed on both ends of the flow channels 19, 20, to form an integrated substrate.

Dimensions of the flow channels 19, 20 and the grooves 21 are the same as those shown in the first embodiment, and formation of the flow channels 19, 20, the grooves 21, the holes 22, 23, 24, 25, and hydrophobization of an inner face of each of the grooves 21 may be conducted in similar manners as described in the first embodiment. Bonding between the silicon substrates 17, 18 may be achieved by hydrofluoric acid bonding utilizing oxide layers which are formed on the surfaces of the silicon substrates.

FIG. 3A to FIG. 3B shows a third embodiment of the double-flow channel type gas exchange chip, in which FIG. 3A is a plan view showing an arrangement of flow channels and grooves, and FIG. 3B is a section view along the line A-A in FIG. 3A.

Substrates 31, 32 are glass substrates, for example, quartz substrates. On one side of one glass substrate 31, a flow channel 33 is formed, and at the positions of both ends of the flow channel 33, through-holes 35, 37 for use in introduction or discharge of a liquid or a gas are formed. On one side of the other glass substrate 32, a flow channel 34 is formed, and at the positions of both ends of the flow channel 34, through-holes 36, 38 for use in introduction or discharge of a liquid or a gas are formed.

A reference numeral 39 denotes a resin membrane in which fine pores are formed to penetrate in the direction of thickness of membrane so that the pores do not cross each other. This membrane 39 is formed by piercing multiple pores having a diameter of not more than 1 μm by irradiating a thin membrane of polycarbonate, for example, with neutrons in the direction perpendicular to the surface, and hydrophobizing at least a part of each of the pores. Hydrophobization may be achieved by fluorinating the inner face of the pores in a similar manner as described in the first embodiment, for example, by an RIE process under flow of a fluorine compound gas such as $CHF_3$ gas or $CF_4$ gas or by decomposition of the fluorine compound by optical irradiation of an excimer laser. In this case, it is not easy to fluorinate inside the pores. However, in the present invention, hydrophobization for preventing immersion of a liquid may be conducted only in entrance parts of the pores. In the present invention, at least a part of the inner face of the groove is hydrophobic is intended to include such a condition.

The glass substrates 31, 32 are intervened by the membrane 39, and opposed so that the faces on which the flow channels 33, 34 are formed are inside, and bonded while they are positioned so that the flow channels 33, 34 are opposed with the membrane 39 interposed therebetween, to form an integrated substrate. Bonding of the glass substrates 31, 32 intervened by the membrane 39 may be achieved by an adhesive.

Dimensions of the flow channels 33, 34 are the same as those shown in the first embodiment, and formation of the flow channels 33, 34 and the holes 35, 36, 37, 38 may be conducted in similar manners as described in the first embodiment.

One exemplary gas extracting method using such a double-flow channel type gas exchange chip is to cause liquids to flow into both flow channels, and transfer gas component in the liquid of one of the flow channels to the liquid of the other flow channel.

When liquids are caused to flow through both of the flow channels, the liquids will not enter the grooves 9, 21 or the pores of the membrane 39, and a gas remains in the grooves 9, 21 or the pores of the membrane 39, so that the gas components contained in the liquids flowing through the flow channels are exchanged via the gas.

In one concrete example, the liquid in one of the flow channels is a sample water containing carbon dioxide, while the liquid in the other flow channel is pure water, and carbon dioxide in the sample water is transferred into the pure water.

Another exemplary gas extracting method using such a double-flow channel type gas exchange chip is to cause a liquid flow into one of the flow channels, and cause a gas to flow into the other flow channel, thereby dissolving the gas into the liquid in one of the flow channels through the grooves 9, 21 or the pores of the membrane 39.

Still another exemplary gas extracting method using such a double-flow channel type gas exchange chip is to cause a liquid flow into one of the flow channels and reduce the pressure of the other flow channel, thereby transferring gas component in the liquid in one of the flow channels into the other one of the flow channels through the grooves 9, 21 or the pores of the membrane 39.

FIG. 4A to FIG. 4B show one embodiment of a single-flow channel type gas exchange chip in which FIG. 4A is a plan view showing an arrangement of a flow channel and grooves, and FIG. 4B is a section view along the line A-A in FIG. 4A.

Reference numerals 40, 41 denote glass substrates, for example, quartz substrates. On one side of one glass substrate 40, a flow channel 42 having a width and a depth of 1000 μm or less, preferably several hundred micrometers or less, is formed. On one side of the other glass substrate 41, multiple grooves 45 having hydrophobic surfaces are formed at positions interlinking the flow channel 42 and externally, and at the positions corresponding to both ends of the flow channel 42, holes 43, 44 for use in introduction or discharge of a liquid or a gas are formed so that they penetrate the glass substrate 41.

The glass substrates 40, 41 face each other so that the surface in which the flow channel 42 is formed and the surface in which the grooves 45 are formed are inside and bonded while they are positioned so that the holes 43, 44 are disposed on both ends of the flow channel 42, and the grooves 45 are bound with the flow channel 42 to form an integrated substrate.

Dimensions of the flow channel 42 are similar to that shown in the first embodiment, and formation of the flow channel 42, the grooves 45, the holes 43, 44, the hydrophobizing process of the grooves 45 and bonding between the substrates 40, 41 may be conducted in similar manners as described in the first embodiment.

The gas exchange chip of the present embodiment may be formed in a silicon substrate.

One exemplary gas extracting method using such a single-flow channel type gas exchange chip is to cause a liquid to flow into the flow channel, and dissolve external gas in the liquid in the flow channel. A concrete example thereof is to extract external carbon dioxide into pure water. In this case, when pure water flows through the flow channel 42, the pure water will not enter the grooves 45, while external carbon dioxide dissolves into the pure water in the flow channel 42 through the grooves 45.

Another exemplary gas extracting method using the single-flow channel type gas exchange chip is to cause a liquid to flow into the flow channel and reduce external pressure, thereby extracting gas components in the liquid in the flow channel outside the substrate.

FIG. 5 shows one embodiment of a total organic carbon measuring instrument using the double-flow channel type gas exchange chip in the embodiment shown in FIG. 1A to FIG. 1B, FIG. 2A to FIG. 2B, or FIG. 3A to FIG. 3B.

The total organic carbon measuring instrument has an organic compound oxidative decomposing part 53 for converting organic carbon in a sample water into carbon dioxide, a carbon dioxide extracting part 55 for extracting carbon dioxide generated in the organic compound oxidative decomposing part 53 into pure water, and a detecting part 56 for measuring conductivity of the pure water from the carbon dioxide extracting part 55 for quantifying carbon dioxide extracted in the carbon dioxide extracting part 55. As the carbon dioxide extracting part 55, a double-flow channel type gas exchange chip in the embodiment shown in FIG. 1A to FIG. 1B, FIG. 2A to FIG. 2B, or FIG. 3A to FIG. 3B is used. A sample water from the organic compound oxidative decomposing part 53 is caused to flow through one of the flow channels in the double-flow channel type gas exchange chip, and pure water is caused to flow through the other one of the flow channels, and the pure water having passed through the gas exchange chip is introduced into the detecting part 56.

In this total organic carbon measuring instrument, for removing carbon dioxide originally dissolved in a sample water, carbon dioxide in the sample water containing an organic compound is removed by adding an acid in an IC (inorganic carbon) removing part 50 and reducing the pressure using a vacuum pump 52 via a hydrophobic porous membrane 51. Carbon dioxide can be removed while preventing dissociation by addition of an acid, although it is difficult to be removed from water because carbon dioxide dissociates in water without added acid.

Then the sample water is fed to the organic compound oxidative decomposing part 53, and the organic compound in the sample water from which carbon dioxide is removed is oxidized by UV energy emitted by an UV lamp 54 and addition of an oxidizing agent or a catalyst (for example, titanium oxide), to be rendered carbon dioxide. The sample water in which carbon dioxide generated by oxidative decomposition of the organic compound is dissolved is then fed to the gas exchange chip of the carbon dioxide extracting part 55 where carbon dioxide contained in the sample water is transferred into pure water. The pure water is fed to the detecting part 56 where concentration of carbon dioxide is determined by measuring conductivity of the pure water.

FIG. 6 shows the measurement results of the depth of the flow channel through which a sample water containing carbon dioxide flows and a migration rate of carbon dioxide in the embodiment of the gas exchange chip shown in FIG. 1A and FIG. 1B. The horizontal axis represents a liquid retention time in the flow channel which is determined by the flow rate and length of the flow channel. It is demonstrated that the smaller the depth of the flow channel, the shorter the time is for carbon dioxide to transfer.

INDUSTRIAL APPLICABILITY

The gas exchange chip of the present invention may be used as a gas exchanger for exchanging gas components between liquids, for removing gas component from a liquid, or for transferring gas component to a gas or another liquid, and a total organic carbon measuring instrument using the gas exchange chip may be used as an analyzer for evaluating organic pollution in water for medicine manufacturing, process water for semiconductor production, cooling water, boiler water, tap water and the like, in particular, in water having little impurities called pure water or ultrapure water.

EXPLANATION OF REFERENCE NUMERALS

Figure 1A:
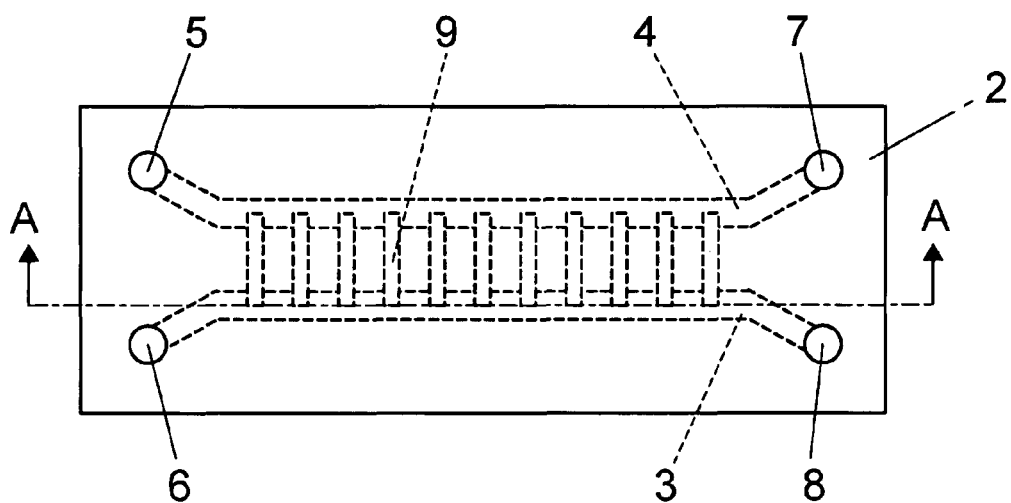
FIG. 1A is a plan view showing an arrangement of flow channels and grooves in a first embodiment of a double-flow channel type gas exchange chip.
Figure 1B:
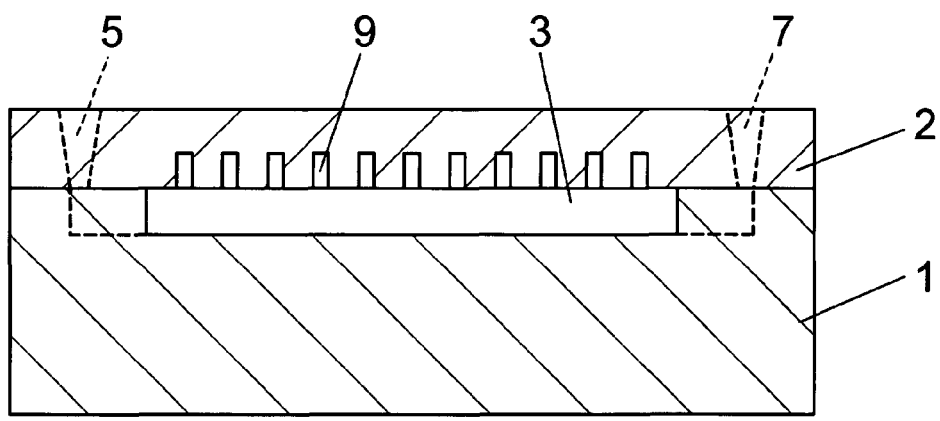
FIG. 1B is a section view along the line A-A in the same embodiment.
Figure 2A:
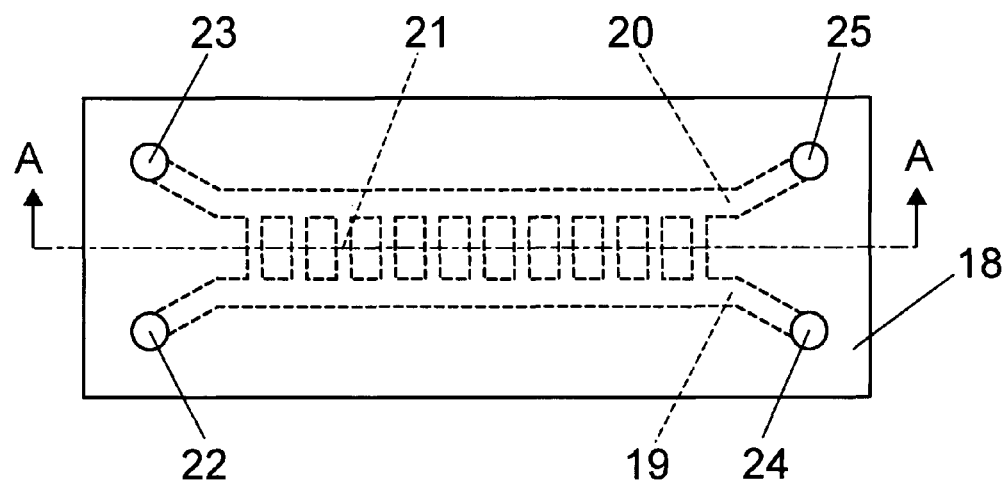
FIG. 2A is a plan view showing an arrangement of flow channels and grooves in a second embodiment of the double-flow channel type gas exchange chip.
Figure 2B:
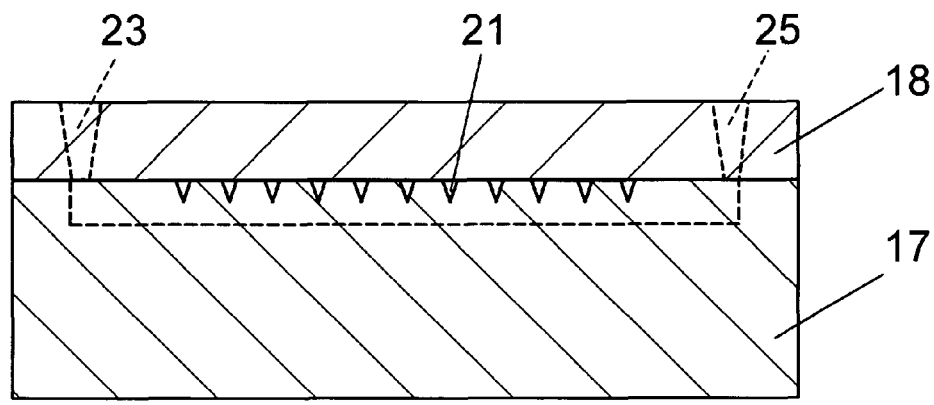
FIG. 2B is a section view along the line A-A in the same embodiment.
Figure 3A:
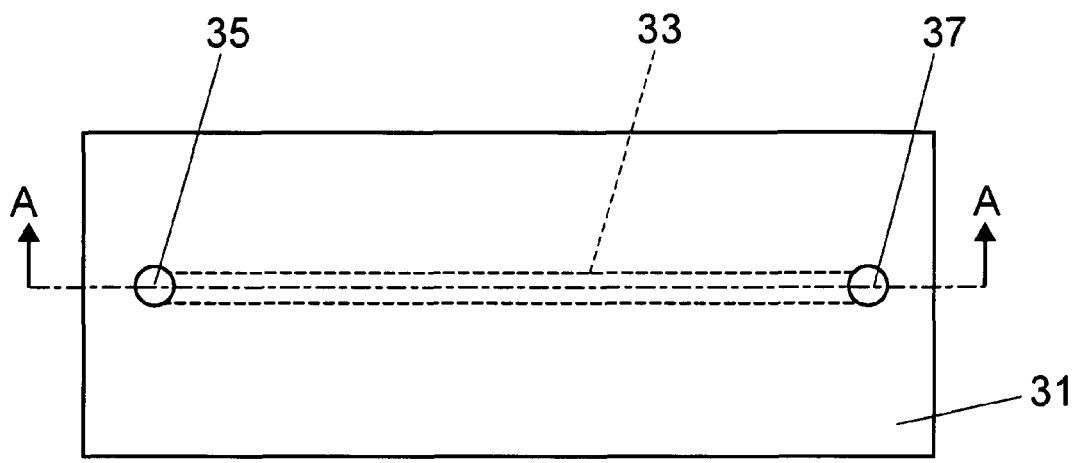
FIG. 3A is a plan view showing an arrangement of flow channels and grooves in a third embodiment of the double-flow channel type gas exchange chip.
Figure 3B:
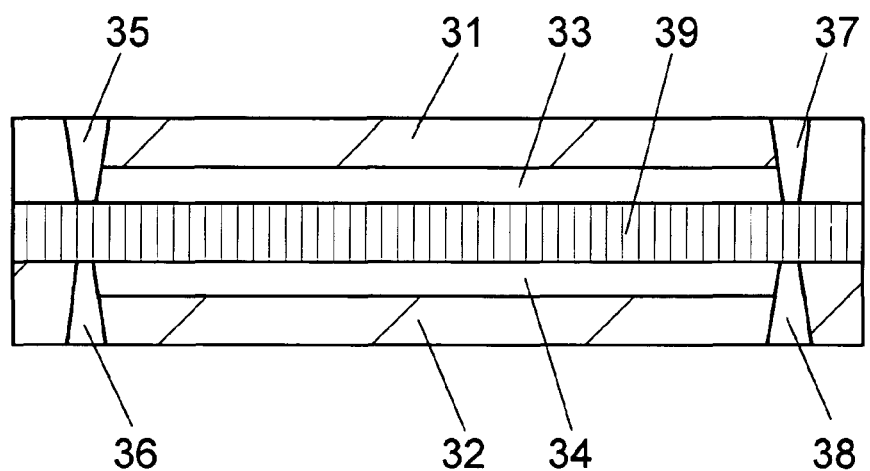
FIG. 3B is a section view along the line A-A in the same embodiment.
Figure 4A:
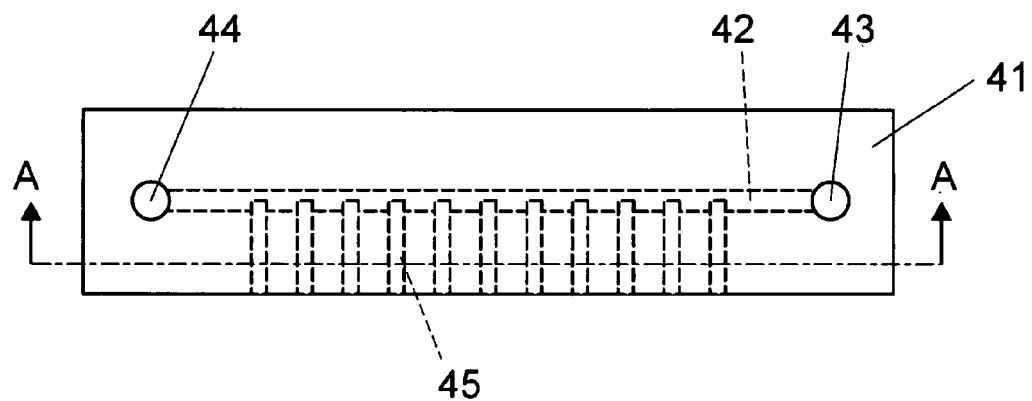
FIG. 4A a plan view showing an arrangement of a flow channel and a groove in one embodiment of a single-flow channel type gas exchange chip.
Figure 4B:
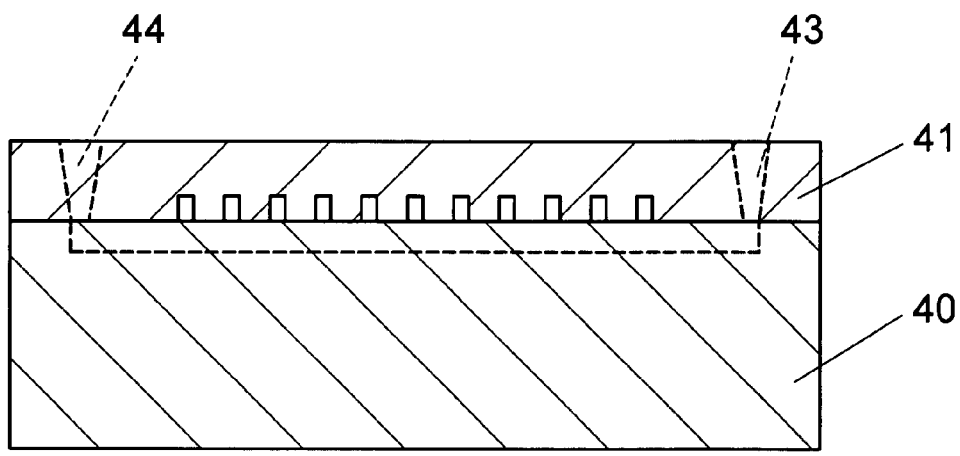
FIG. 4B a section view along the line A-A in the same embodiment.
Figure 5:
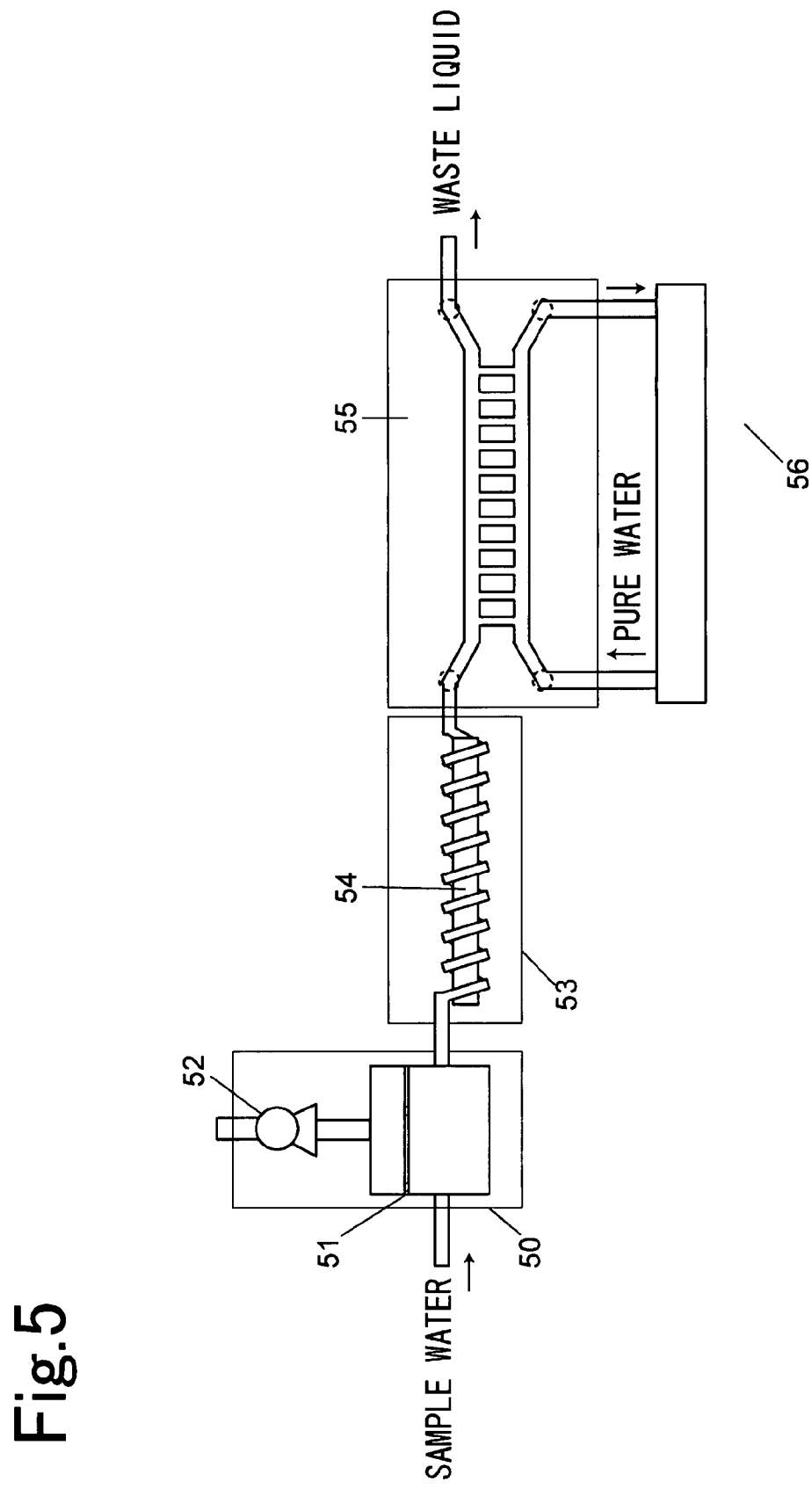
FIG. 5 is a schematic structural view showing one embodiment of a total organic carbon measuring instrument.
Figure 6:
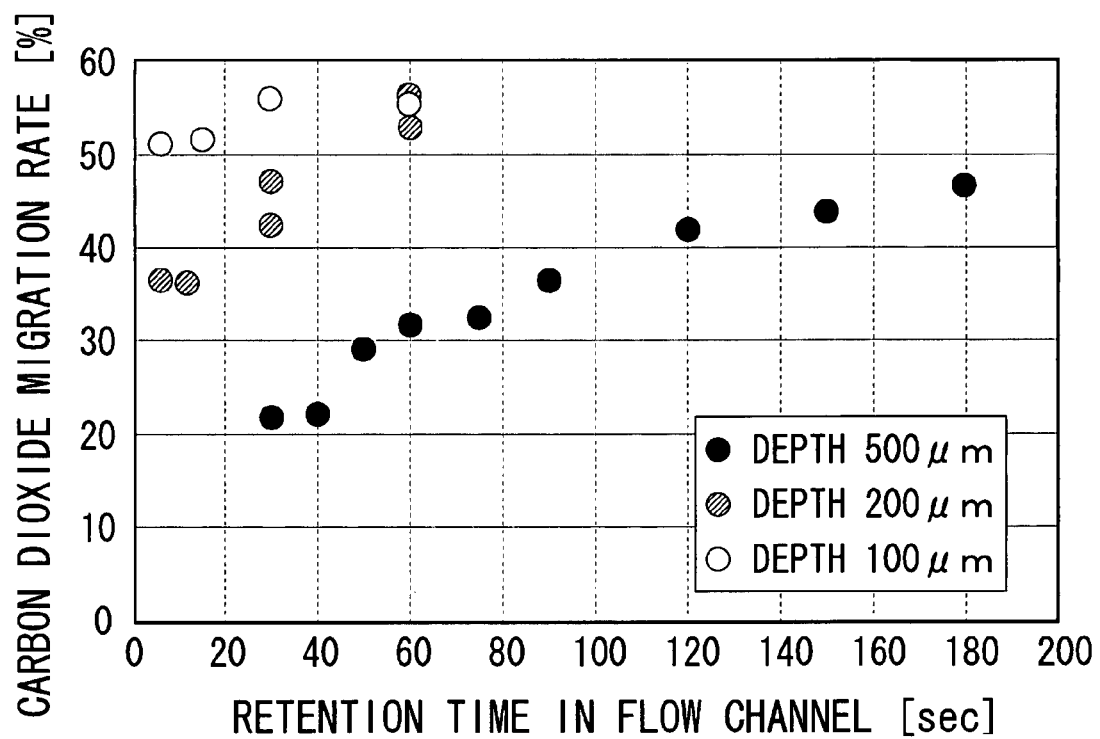
FIG. 6 is a graph showing a depth of a flow channel through which a sample water containing carbon dioxide flows, and a migration rate of carbon dioxide in one embodiment of the gas exchange chip.

1, 2, 31, 32, 40, 41 glass substrate
3, 4, 19, 20, 33, 34, 42 flow channel
9, 21, 45 groove
5, 6, 7, 8, 22, 23, 24, 25, 35, 36, 37, 38, 43, 44 hole
39 membrane
50 IC removing part
53 organic compound oxidative decomposing part
55 carbon dioxide extracting part
56 detecting part

What is claimed is:

1. A gas exchange chip comprising:
   a substrate;
   two flow channels formed in the substrate, each flow channel flowing a liquid and having an inlet port and an outlet port; and
   multiple grooves interlinking the two flow channels,
   wherein the grooves are formed in the substrate, and
   wherein at least a part of an inner face of each of the grooves is hydrophobized and a size of a cross section of each of the grooves is adapted to permit passage of gas component while inhibiting any liquid entering.

2. The gas exchange chip according to claim 1, wherein a depth and a width of the flow channel(s) are 1000 μm or less.

3. The gas exchange chip according to claim 1, wherein a depth and a width of each of the grooves are 10 μm or less.

4. The gas exchange chip according to claim 1, wherein a diameter of each of the grooves is 1 μm or less.

5. The gas exchange chip according to claim 1, wherein the grooves are formed in such orientation that they do not cross each other.

6. The gas exchange chip according to claim 1, wherein the two flow channels are disposed parallel to each other in a plane which is parallel to the surface of the substrate.

* * * * *